United States Patent
Wang et al.

(12) 
(10) Patent No.: US 6,303,537 B1
(45) Date of Patent: Oct. 16, 2001

(54) VINYL ACETATE CATALYST COMPRISING METALLIC PALLADIUM AND GOLD AND PREPARED UTILIZING SONICATION

(75) Inventors: Tao Wang; Jerry A. Broussard; H. Robert Gerberich, all of Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 09/441,603

(22) Filed: Nov. 17, 1999

(51) Int. Cl.⁷ .............................. B01J 23/58; B01J 23/40; B01J 23/42; B01J 23/56; B01J 23/44
(52) U.S. Cl. ..................... 502/330; 502/327; 502/332; 502/333; 502/339; 502/344
(58) Field of Search .................................. 502/327, 330, 502/332, 333, 339, 344, 355

(56) References Cited

U.S. PATENT DOCUMENTS

| | | | |
|---|---|---|---|
| 3,775,342 | 11/1973 | Kronig et al. | 252/430 |
| 3,822,308 | 7/1974 | Kronig et al. | 260/497 |
| 4,048,096 * | 9/1977 | Bissot | 252/430 |
| 4,087,622 * | 5/1978 | Nakamura et al. | 560/245 |
| 4,136,062 * | 1/1979 | Boudart et al. | 252/460 |
| 5,274,181 * | 12/1993 | Bartley et al. | 560/245 |
| 5,314,858 * | 5/1994 | Colling | 502/330 |
| 5,332,710 | 7/1994 | Nicolau et al. | 502/243 |
| 5,347,046 | 9/1994 | White et al. | 560/245 |
| 5,466,652 * | 11/1995 | Paparizos et al. | 502/330 |
| 5,536,693 * | 7/1996 | Lemanski et al. | 502/300 |
| 5,559,071 * | 9/1996 | Abel et al. | 502/326 |
| 5,567,839 * | 10/1996 | Gulliver et al. | 560/245 |
| 5,591,688 * | 1/1997 | Blum et al. | 502/330 |
| 5,622,908 * | 4/1997 | Abel et al. | 502/339 |
| 5,665,667 * | 9/1997 | Lemanski et al. | 502/300 |
| 5,672,734 * | 9/1997 | Abel et al. | 560/245 |
| 5,674,800 * | 10/1997 | Abel et al. | 502/326 |
| 5,691,267 * | 11/1997 | Nicolau et al. | 502/330 |
| 5,693,586 * | 12/1997 | Nicolau et al. | 502/330 |
| 5,700,753 | 12/1997 | Wang et al. | 502/330 |
| 5,705,679 * | 1/1998 | Nicolau et al. | 560/245 |
| 5,731,457 * | 3/1998 | Nicolau et al. | 560/245 |
| 5,777,156 * | 7/1998 | Abel et al. | 560/245 |
| 5,783,726 * | 7/1998 | Lemanski et al. | 560/261 |
| 5,854,171 * | 12/1998 | Nicolau et al. | 502/330 |
| 5,859,287 * | 1/1999 | Nicolau et al. | 560/241 |
| 5,948,724 * | 9/1999 | Nicolau et al. | 502/331 |
| 5,968,860 * | 10/1999 | Herzog | 502/5 |
| 5,968,869 * | 10/1999 | Nicolau et al. | 502/300 |
| 5,972,824 * | 10/1999 | Herzog et al. | 502/160 |
| 6,015,769 * | 1/2000 | Wang | 502/331 |
| 6,017,847 * | 1/2000 | Wang | 502/331 |
| 6,022,823 * | 2/2000 | Augustine et al. | 502/243 |
| 6,034,030 * | 3/2000 | Nicolau et al. | 502/326 |
| 6,057,260 * | 5/2000 | Nicolau et al. | 502/331 |
| 6,072,078 * | 6/2000 | Nicolau et al. | 560/245 |
| 6,107,513 * | 8/2000 | Herzog et al. | 560/208 |
| 6,107,514 * | 8/2000 | Nicolau et al. | 560/245 |
| 6,114,573 * | 9/2000 | Herzog | 560/261 |

OTHER PUBLICATIONS

Suslick, K.8., "Organometallic Sonochemistry," Advances in Organometallic Chemistry 25, 73–199 (1986).

Suslick, K.S.; Fang, M.; Hyeon, T.; and Cichowlas, A.A., "Nanostructured Fe–Co Catalysts Generated by Ultrasound," Materials Research Society Symposia Proceedings, 351, 443–448 (1994).

Okitsu, K.; Bandow, H.; and Maeda, Y.; "Sonochemical Preparation of Ultrafine Palladium Particles," Chemistry of Materials 8, 315–317 (1996).

* cited by examiner

*Primary Examiner*—Steven P. Griffin
*Assistant Examiner*—Cam N. Nguyen

(57) ABSTRACT

A catalyst effective for the production of vinyl acetate by reaction of ethylene, oxygen and acetic acid, comprising a porous support on the porous surfaces of which is deposited catalytically effective amounts of metallic palladium and gold, and prepared by steps comprising impregnating the support with one or more aqueous solutions of water-soluble compounds of the metals, fixing the metals on the support as water-insoluble compounds in one or more fixing steps by reaction with an appropriate alkaline compound, and reducing the water-insoluble compounds of the catalytically active metals to their free metallic form in one or more reducing steps, at least one of the said reducing steps being carried out in an aqueous medium containing a reducing agent dissolved therein or through which a gaseous reducing agent is bubbled, and in which the support containing the fixed water-insoluble metal compounds is immersed, while sonicating, i.e., applying ultrasound waves to, such aqueous medium.

8 Claims, No Drawings

US 6,303,537 B1

VINYL ACETATE CATALYST COMPRISING METALLIC PALLADIUM AND GOLD AND PREPARED UTILIZING SONICATION

BACKGROUND OF THE INVENTION

1. Field of the Invention

The invention relates to new and improved catalysts comprising metallic palladium and gold, which are useful for the production of vinyl acetate by reaction of ethylene, oxygen and acetic acid.

2. Description of the Related Art

It is known to produce vinyl acetate by reaction of ethylene, oxygen and acetic acid using a catalyst comprising palladium and gold, supported on a carrier. While the process utilizing such a catalyst is capable of producing vinyl acetate at relatively high levels of productivity, any expedient which could possibly result in even greater productivity or a decrease in by products would be very desirable.

The following references may be considered material to the invention claimed herein.

U.S. Pat. No. 3,775,342 issued Nov. 27, 1973, and U.S. Pat. No. 3,822,308 issued Jul. 2, 1974, both to Kronig et al., each discloses a method of making vinyl acetate catalysts comprising treating a support simultaneously or successively with a solution A containing dissolved salts of noble metals such as palladium and gold and a solution B containing compounds able to react on the support with the noble metal salts to form water-insoluble compounds, treating such water-insoluble compounds with a reducing agent to convert the water-insoluble noble metal compounds to the free metals, washing the catalyst to remove water-soluble compounds, and applying an alkali metal compound, e.g., an alkali metal carboxylate before or after treatment with the reducing agent. Solution A can optionally also contain salts of other metals such as magnesium, calcium, barium and copper.

U.S. Pat. No. 5,322,710, issued Jul. 26, 1994, to Nicolau et al., discloses a method of preparing a catalyst useful for the production of vinyl acetate by reaction of ethylene, oxygen and acetic acid, comprising impregnating a porous support with water soluble salts of palladium and gold, fixing the palladium and gold as insoluble compounds on the support by immersing and tumbling the impregnated support in a reactive solution for at least ½ hour to precipitate such compounds, and subsequently reducing the compounds to free metallic form.

U.S. Pat. No. 5,347,046, issued Sept. 13, 1994 to White et al., discloses catalysts for the production of vinyl acetate by reaction of ethylene, oxygen, and acetic acid, comprising a palladium group metal and/or a compound thereof, gold and/or a compound thereof, and copper, nickel, cobalt, iron, manganese, lead or silver, or a compound thereof, preferably deposited on a support material.

Suslick, K. S., "Organometallic Sonochemistry," *Advances in Organometallic Chemistry* 25, 73–119 (1986) is a general article on the application of ultrasound waves to organometalic reactions.

Suslick, K. S.; Fang, M.; Hyeon, T.; and Cichowlas, A. A., "Nanostructured Fe-Co Catalysts Generated by Ultrasound," *Materials Research Society Symposia Proceedings*, 351, 443–448 (1994), discuss the preparation and activity of Fe-Co catalysts generated with ultrasound waves.

Okitsu, K.; Bandow, H.; and Maeda, Y.; "Sonochemical Preparation of Ultrafine Palladium Particles," *Chemistry of Materials* 8, 315–317 (1996) discuss the sonochemical reduction of Pd (II) in the presence of protective agents such as surfactants to produce ultrafine Pd particles and state that colloidal dispersion of these particles "exhibit interesting catalytic activity."

BRIEF SUMMARY OF THE INVENTION

In accordance with this invention, a catalyst effective for the production of vinyl acetate by reaction of ethylene, oxygen and acetic acid, comprising a porous support on the porous surfaces of which is deposited catalytically effective amounts of metallic palladium and gold, and optionally, one or more additional catalytically active metals, is prepared by steps comprising impregnating the support with one or more aqueous solutions of water-soluble compounds of the metals, fixing the metals on the support as water-insoluble compounds in one or more fixing steps by reaction with an appropriate alkaline compound, and reducing the water-insoluble compounds of the catalytically active metals to their free metallic form in one or more reducing steps, at least one of such reducing steps being carried out in an aqueous medium containing a reducing agent dissolved therein or through which a gaseous reducing agent is bubbled, and in which the support containing the fixed water-insoluble metal compounds is immersed while sonicating, i.e., applying ultrasound waves to, such aqueous medium.

Catalysts may be prepared by the method of this invention utilizing sonication in the reducing step, which are capable of implementing the production of vinyl acetate by reaction of ethylene, oxygen and acetic acid with somewhat reduced selectivities to $CO_2$ and/or heavy ends such that the use of such catalysts may result in greater vinyl acetate productivity than when any of various catalysts known in the art is employed.

DETAILED DESCRIPTION OF THE INVENTION

In preparing the catalysts under this invention, the catalyst support material is composed of particles having any of various regular or irregular shapes, such as spheres, tablets, cylinders, rings, stars, or other shapes, and may have dimensions such as diameter, length, or width of about 1 to about 10 mm., preferably about 3 to 9 mm. Spheres having a diameter of about 4 to about 8 mm. are preferred. The support material may be composed of any suitable porous substance, e.g., silica, alumina, silica-alumina, titania, zirconia, silicates, aluminosilicates, titanates, spinel, silicon carbide, or carbon and the like.

The support material may have a surface area within the range, for example, of about 10 to about 350, preferably about 100 to about 200 $m^2/g$, an average pore size in the range, for example, of about 50 to about 2000 angstroms, and a pore volume in the range, for example, of about 0.1 to 2, preferably about 0.4 to about 1.2 ml/g.

In the preparation of the catalysts of this invention, the support material may be treated to deposit catalytic amounts of palladium, gold, and any additional catalytically active metal, if any, on the porous surfaces of the support particles. Any of various methods for accomplishing this purpose may be used, all of which involve simultaneous or separate impregnations of the support with one or more aqueous solutions of water-soluble compounds of the catalytically active metals. Palladium(II)chloride, sodium palladium(II) chloride, potassium palladium(II)chloride, palladium(II) nitrate or palladium(II)sulfate are examples of suitable water-soluble palladium compounds; and an alkali metal, e.g., sodium or potassium salt of auric(III)chloride or tetrachloroauric(III)acid can be used as the water-soluble gold compound. An alkali metal salt of tetrachloroauric(III) acid and sodium palladium(II)chloride are preferred salts for impregnation of gold and palladium respectively because of their good water solubility.

In preparing the catalyst, the impregnations of the support material with solutions of water-soluble salts of the catalytically active metals may be effected by any method known to those skilled in the art. Preferably, however, such impregnations are accomplished by the "incipient wetness" method wherein an amount of water-soluble salt solution used for the impregnation is from about 95 to about 100 percent of the absorptive capacity of the support material. The concentration of the solution or solutions is such that the amounts of catalytically active metals in the solution or solutions absorbed on the support is equal to a desired predetermined amount. If more than one such impregnation is carried out, then each impregnation may contain water soluble compound equivalent to all or only a portion of the amount of one or any combination of the catalytically active metals desired in the final catalyst, as long as the amounts of such metals in the total of the impregnating solutions absorbed are equal to the final desired amounts. The impregnations are such as to provide, for example, about 1 to about 10 grams of elemental palladium; and, for example, about 0.5 to about 10 grams of elemental gold per liter of finished catalyst, with the amount of gold being from about 10 to about 125 weight percent based on the weight of palladium.

After each impregnation of the support with an aqueous solution of at least one water-soluble salt of a catalytically active metal, the metal is "fixed," i.e., precipitated, as a water-insoluble compound such as the hydroxide, by reaction with an appropriate alkaline compound, e.g., an alkali metal hydroxide, silicate, borate, carbonate or bicarbonate, in aqueous solution. Sodium and potassium hydroxides are preferred alkaline fixing compounds. The alkaline compound should be in an amount of, for example, about 1 to about 2, preferably about 1.1. to about 1.8 times the amount necessary to completely precipitate the cations of the catalytically active metals present in the water-soluble salts- The fixing of the metals may be done by the incipient wetness method wherein the impregnated support is dried, e.g., at a temperature of about 150° C. for one hour, contacted with an amount of solution of the alkaline material equal to about 95–100% of the pore volume of the support, and allowed to stand for a period of about ½ hour to about 16 hours; or the roto-immersion method wherein the impregnated support without drying is immersed in a solution of the alkaline material and is rotated and/or tumbled during at least the initial period of precipitation such that a thin band of the precipitated water-soluble compound is formed at or near the surface of the support particles. In carrying out the fixing of metals by roto-immersion, the rotation and tumbling may be carried out, for example, at about 1 to about 10 rpm for a period of, for example, at least about 0.5 hour, preferably about 0.5 to about 4 hours. The contemplated roto-immersion method is disclosed in previously cited U.S. Pat. No. 5,332,710, the entire disclosure of which is incorporated herein by reference.

The fixed, i.e. precipitated compounds of palladium, gold, and other catalytically active metals, if any, may be reduced in one or more reducing steps. At least one of such reducing steps is accomplished with the aid of sonication, i.e., the application of ultrasound waves to an aqueous solution of the reducing agent, or an aqueous medium through which a gaseous reducing agent is bubbled, in either of which is immersed the support material containing on its surfaces at least one fixed water-insoluble compound of a catalytically active metal. Reducing agents which can be used to reduce the fixed water-insoluble compounds of the catalytically active metals, including palladium and gold to their free metallic form, in conjunction with sonication are those well-known in the art as reducing agents for the purpose including gases, e.g., a lower alkene such as ethylene, or hydrogen, which is bubbled through the aqueous medium in which is immersed the support containing the fixed water-insoluble compounds during sonication, and water-soluble reducing agents such as hydrazise which is dissolved in the aqueous medium in which is immersed the support containing the fixed compounds during sonication. In addition to these, however, other reducing agents can be used in conjunction with sonication, e.g., protective agents such as surfactants, including anionic surfactants, e.g., alkali metal salts of sulfated $C_{10}$–$C_{18}$ primary or secondary monohydric alcohols such as sodium dodecyl sulfate (SDS) and nonionic surfactants such as esters of an oxyethylated polyhydric alcohol or polyethylene glycol with a $C_8$–$C_{20}$ carboxylic acid, containing about 5 to about 50 oxyethylene groups, e.g. poly(oxyethylene (20) sorbitan monolaurate) (commonly referred to as Tween 20) and poly(ethylene (40) glycol monostearate) (PEG40-MS); and water-soluble polymers such as poly(vinylpyrrolidone).

In catalyst preparations including more than one reducing step, one or all of the reducing steps may be carried out utilizing sonication. However, if less than all of the reducing steps employ sonication, then the reducing steps other than those employing sonication may be done, for example, in the vapor phase with ethylene, e.g., about 5% in nitrogen at about 150° C. for about 5 hours after first washing the catalyst containing the fixed metal compounds, until it is free of anions such as halide, and drying, e.g., at about 150° C. for about 1 hour, or such reduction may be accomplished before washing and drying in the liquid phase at room temperature with an aqueous solution of hydrazine hydrate wherein the excess of hydrazine over that required to reduce all the metal compounds present on the support is in the range, for example, of about 8:1 to about 15:1, followed by washing and drying. Other reducing agents and means for reducing the fixed metal compounds present on the support may be employed as conventional in the art.

The reduction of the fixed palladium, gold and other metal compounds, if any, whether or not sonication is employed, mainly results in the formation of the free metal, although a minor amount of metal oxide may also be present. In preparations using more than one impregnation and fixing steps, the reduction may be carried out after each fixing step or after the total of the metallic elements have been fixed on the support. In addition to being utilized in one or more reducing steps as described previously, sonication may also be utilized in one or more fixing steps, e.g., by applying the sonication to water containing immersed therein the catalyst support containing the impregnated (water-soluble) metal compound.

A simple example of carrying out the foregoing catalyst preparation includes a single impregnation of the support with water soluble salts such that the impregnated support contains the palladium and gold desired in the final catalyst, a single fixing step by incipient wetness, roto-immersion or sonication as described previously, and a single reducing step whereby the fixed palladium and gold are reduced to their free metallic form utilizing sonication as described previously.

As another example of the foregoing general procedure, a "separate fix" method may be used to fix the catalytically active metallic elements on the support and reduce the water-insoluble metal compounds to the desirable free metallic form. In this method, using the specific procedures described previously, the support is first impregnated with an aqueous solution of a water-soluble compound of palladium and of any additional catalytically active metal, if any, other than gold, and the palladium, and additional metal, if present, are then fixed by treatment with an alkaline fixing solution using incipient wetness, roto-immersion or sonication. The catalyst is then dried and separately impregnated with a solution of a soluble gold compound having the amount of elemental gold desired in the catalyst, and the gold is fixed by treatment with an alkaline fixing solution as described. If the gold is to be fixed by the incipient wetness method, such fixing may be combined with the impregnation step by using a single aqueous solution of soluble gold compound and alkaline fixing compound in an amount in excess of that necessary to convert all the gold in the solution to a fixed insoluble gold compound, e.g., auric hydroxide. The fixed water-insoluble compounds of the catalytically active metals are then reduced utilizing sonication, as described previously.

After the catalyst containing palladium, gold and any additional catalytically active metal, if any, in a free metallic form, deposited on a support material, is prepared by any of the foregoing methods, it is advantageously further impregnated with a solution of an alkali metal acetate, preferably potassium or sodium acetate, and most preferably potassium acetate. The catalyst is then dried such that the finished catalyst contains, for example, about 10 to about 70, preferably about 20 to about 60 grams of alkali metal per liter of finished catalyst.

When vinyl acetate is prepared using a catalyst according to the present invention, a stream of gas, which contains ethylene, oxygen or air, acetic acid, and desirably an alkali metal acetate, is passed over the catalyst. The composition of the gas stream can be varied within wide limits, taking into account explosive limits. For example, the molar ratio of ethylene to oxygen can be about 80:20 to about 98:2, the molar ratio of acetic acid to ethylene can be about 2:1 to about 1:10, preferably about 1:1 to about 1:5, and the content of gaseous alkali metal acetate can be about 1–100 ppm, relative to the acetic acid employed. The alkali metal acetate may be conveniently added to the feed stream as a spray of an aqueous solution of such acetate. The gas stream also can contain other inert gases, such as nitrogen, carbon dioxide and/or saturated hydrocarbons. Reaction temperatures which can be used are elevated temperatures, preferably those in the range of about 150–220° C. The pressure employed can be a somewhat reduced pressure, normal pressure or elevated pressure, preferably a pressure of up to about 20 atmospheres gauge.

The following non-limiting examples further illustrate the invention. In each example, the sonication was carried out in a 250-ml round bottom sonication flask (Misonix) with three 24/40 side necks using an XL2020 Sonicator Programmable Ultrasonic Processor (Misonix) fitted with a flat-tipped tapped disrupter horn (titanium alloy, ¾" diameter). The ultrasound waves emitted by the sonicator had a frequency of 20 kHz. Sonication was carried out for about 1 hour to about 20 hours. The sonication may be effected by any of the various types of sonicators known in the art, several of which are commercially available. The support material for the catalyst consisted of Sud Chemie KA-160 silica spheres having a nominal diameter of 5 mm., a surface area of about 160 to 175 m$^2$/g, and a pore volume of about 0.68 ml/g.

EXAMPLES

Example 1

100 cc of the 5 mm silica support material for the catalyst was measured into a 500-ml round bottom flask. In a 100-ml graduated cylinder, aqueous Na$_2$PdCl$_4$ (7 g Pd/i support), aqueous NaAuCl$_4$ (4 g Au/i support), and deionized water were added to produce a total solution volume equal to the total volume the support could absorb. The Pd/Au-containing solution was poured into the silica support to impregnate the support by incipient wetness, and the support was shaken for approximately 5 minutes to ensure complete absorption of the solution. The treated support was then poured into a 1000-ml pear-shaped flask containing 114 cc of aqueous NaOH (from 50% w/w NaOH/H$_2$O, 120% of the amount of NaOH needed to convert the metal salts to their hydroxides). The flask was immediately placed on the rotovap (rotary evaporator) to rotate for 2.5 hours at approximately 5 rpm. The solution was drained from the treated support, and the treated support was poured in a 500-ml graduated cylinder with dip tube to wash with a continuous flow of deionized water for 5 hours. The effluent was tested with AgNO$_3$ to detect the presence of chlorides via formation of insoluble AgCl. The effluent was drained from the treated support, and the treated support was transferred into a sonication flask containing 114 cc of deionized H$_2$O. One of the necks of the flask was plugged with a septum, another with a septum containing a sparger hooked to a gas inlet line, and the third with a glass stopper containing a gas outlet line. The sparger was placed under the surface of the water, and N$_2$ was bubbled through the sparger at a flow rate of 0.5 SCFH for 2 hours. As the N$_2$ was turned off, the 5% C$_2$H$_4$ in N$_2$ was turned on to a flow rate of 0.5 SCFH. The sonicator was immediately turned on, and the support-containing water was sonicated at level 1 for 14 hours.

After sonication, the water was drained from the support, and the support was transferred to a 500-ml round bottom flask to dry overnight at 150° C. under constant N$_2$ purge. KOAc (40 g/l support) and deionized water were added to a 100-ml graduated cylinder to produce a solution volume equal to the amount of solution the support would absorb. The treated support was impregnated by incipient wetness with the aqueous KOAc and let stand for 15 minutes. The catalyst was transferred to a fluid-bed dryer to dry for 1 hour at 100° C.

Example 2

The procedure of Example 1 was followed except that the reduction was carried out via sonication at level 1 for 23 hours.

Example 3

The procedure of Example 1 was followed except that the reduction was carried out via sonication at level 1 for 11 hours.

Example 4

The procedure of Example 1 was followed except that the reduction was carried out via t sonication at level 1 for 7 hours.

Example 5

The procedure of Example 1 was followed except that the support contained 7g Au/l and the reduction was carried out via sonication at level 1 for 6.5 hours.

Example 6

The procedure of Example 1 was followed except that the support contained 7g Au/l and the reduction was carried out via sonication at level 1 for 7.5 hours.

Example 7

125 cc of the 5 mm p silica catalyst support material was measured into a 500-ml bottom flask. In a 100-ml graduated cylinder, aqueous $Na_2PdCl_4$ (7 g Pd/l support), aqueous $NaAuCl_4$ (7 g Au/l support), and deionized water were added to produce a total solution volume equal to the total volume the support could absorb. The Pd/Au-containing solution was poured into the silica support to impregnate the support by incipient wetness, and the support was shaken for approximately 5 minutes to ensure complete absorption of the solution. The treated support was then poured into a 1000-ml pear-shaped flask containing 142 cc of aqueous NaOH (from 50% W/W $NaOH/H_2O$, 120% of the amount needed to convert the metal salts to their hydroxides). The flask was immediately placed on the rotovap to rotate for 2.5 hours at approximately 5 rpm.

The solution was drained from the treated support, and the treated support was poured in a 500 ml graduated cylinder with a dip tube to wash with a continuous flow of deionized water for 5 hours. The effluent was tested with $AgNO_3$ to detect the presence of chlorides via formation of insoluble AgCl. The effluent was drained from the treated support, and the treated support was transferred into a sonication flask containing 3.7 g SDS (sodium dodecyl sulfate) in 142 cc of deionized $H_2O$. One of the necks of the flask was plugged with a septum, another with a septum containing a sparger hooked to a gas inlet line, and the third with a glass stopper containing a gas outlet line. The sparger was placed under the surface of the water, and $N_2$ was bubbled through the sparger at a flow rate of 0.5 SCFH. The sonicator was immediately turned on, and the treated support-containing SDS was sonicated at a level 1 for 7 hours. After sonication, the solution was drained from the treated support, and the treated support was poured in a 500-ml graduated cylinder with dip tube to wash with a continuous flow of deionized water for 5 hours. The catalyst was transferred to a 500-ml round bottom flask to dry overnight at 150° C. under constant $N_2$ purge. Impregnation with KOAc was carried out following the procedure of Example 8

The procedure of Example 7 was followed except that the reduction was carried out via sonication at level 1 for 7.5 hours.

Example 9

The procedure of Example 7 was followed except that 2 g of Tween 20 was added in place of the 3.7 g of SDS and the reduction was carried out via sonication at level 1 for 7.5 hours.

The catalysts of the examples were tested for their selectivity to various byproducts in the production of vinyl acetate by reaction of ethylene, oxygen and acetic acid. To accomplish this, about 60 ml of each type of catalyst prepared in the examples were placed in separate stainless steel baskets. The temperature of each basket was measured by a thermocouple at both the top and bottom of each basket. Each reaction basket was placed in a Berty continuously stirred tank reactor of the recirculating type (also termed the "VAST," i.e., vinyl acetate stirred tank reactor) and was maintained at a temperature which provided about 45% oxygen conversion with an electric heating mantle. A gas mixture of about 130 l/hr (measured at N.T.P) of ethylene, about 26 l/hr of oxygen, about 128 l/hr of nitrogen, about 130 g/hr of acetic acid, and about 2 mg/hr of potassium acetate, was caused to travel under pressure at about 12 atmospheres through each basket. The reaction was terminated after about 18 hours. Analysis of the products was accomplished by on-line gas chromatographic analysis combined with off-line liquid product analysis by condensing the product stream at about 10° C. to obtain optimum analysis of the end products.

Table I shows for each example details of the method of making the catalyst and its make-up, in terms of the nominal amounts, i.e., total of the catalytically active metals Pd and Au, impregnated onto the support (Metal Content of Catalyst, Nominal Amount), the percentage of the amount of each metal initially impregnated onto the support and retained in the final catalyst (Metal Content of Catalyst, % Retention), the period of time of sonication applied to each reduction of the metals on the catalyst (Sonication, t., hr.), at an intensity level of 1 in all examples, and the reducing agent (Red. Agent) used for the reduction, and details of the process of synthesizing VA from the components of the gaseous feed in terms of the selectivity to $CO_2$, heavy ends (HE), and ethyl acetate (EtOAc). The relative activity of the reaction expressed as an activity factor (Activity) is also shown in Table I and is computer calculated. The computer program uses a series of equations that correlates the activity factor with the catalyst temperature (during the reaction), oxygen conversion, and a series of kinetic parameters for the reactions that take place during VA synthesis. More generally, the activity factor is inversely related to the temperature required to achieve constant oxygen conversion.

TABLE I

VAST UNIT PERFORMANCE DATA FOR CATALYSTS
WHEREIN REDUCTION CONDUCTED WITH SONICATION

| | Metal Content of Catalyst | | | | | | | | | |
|---|---|---|---|---|---|---|---|---|---|---|
| | Nominal Amount g/l | | % Retention | | Sonication | Red. | Selectivity, % | | | |
| Ex. | Pd | Au | Pd | Au | t, hr. | Agent | $CO_2$ | HE | EtOAc | Activity |
| 1 | 7 | 4 | 91 | 68 | 14 | $C_2H_4$ | 8.67 | 0.855 | 0.05 | 1.97 |
| 2 | 7 | 4 | 93 | 73 | 23 | $C_2H_4$ | 9.17 | 0.986 | 0.071 | 1.79 |
| 3 | 7 | 4 | 83 | — | 11 | $C_2H_4$ | 9.02 | 0.991 | 0.068 | 1.76 |
| 4 | 7 | 4 | 95 | 52 | 7 | $C_2H_4$ | 8.66 | 0.906 | 0.080 | 1.76 |
| 5 | 7 | 7 | 81 | 87 | 6.5 | $C_2H_4$ | 9.25 | 1.244 | 0.056 | 1.92 |
| 6 | 7 | 7 | 79 | 50 | 7.5 | $C_2H_4$ | 9.50 | 1.045 | 0.074 | 1.97 |
| 7 | 7 | 7 | 83 | 66 | 6 | SDS | 10.1 | 0.82 | 0.063 | 1.69 |

TABLE I-continued

VAST UNIT PERFORMANCE DATA FOR CATALYSTS
WHEREIN REDUCTION CONDUCTED WITH SONICATION

| | Metal Content of Catalyst | | | | | | Selectivity, % | | | |
|---|---|---|---|---|---|---|---|---|---|---|
| | Nominal Amount g/l | | % Retention | | Sonication t, hr. | Red. Agent | | | | |
| Ex. | Pd | Au | Pd | Au | | | $CO_2$ | HE | EtOAc | Activity |
| 8 | 7 | 7 | 83 | 52 | 7.5 | SDS | 9.64 | 1.297 | 0.060 | 2.11 |
| 9 | 7 | 7 | 86 | 31 | 7.5 | Tween 20 | 9.63 | 1.241 | 0.080 | 1.95 |

The results shown in Table I establish that the supported Pd and Au containing catalysts prepared by a method utilizing sonication in the reduction step are effective in the production of VA by reaction of ethylene, oxygen and acetic acid. In particular, the results of Examples 1–5 that the catalyst made by the method of this invention is capable of catalyzing the reaction with a $CO_2$ selectivity somewhat below that resulting from the use of prior art catalyst. For example, Bayer VA catalysts of the type described in GB 1,246,015 U.S. Pat. No. 5,700,753; incorporated by reference herein. VAST unit performance data for Bayer catalyst was found to be:

| | |
|---|---|
| % $CO_2$ Selectivity | 9.51 |
| % HE Selectivity | 0.89 |
| % EtOAc Selectivity | 0.06 |
| Catalyst Activity | 1.37 |

What is claimed is:

1. A method for the preparation of a catalyst effective for the production of vinyl acetate by reaction of ethylene, oxygen and acetic acid, comprising the steps of impregnating a porous support with one or more aqueous solutions, of water-soluble compounds of catalytically active metals including palladium and gold, fixing said metals on the support as water-insoluble compounds in one or more fixing steps by reaction with an appropriate alkaline compound, and reducing said water-insoluble compounds to their free metallic form in one or more reducing steps, at least one of said reducing steps being carried out in an aqueous medium containing a reducing agent in which the support containing said fixed water-insoluble compounds is immersed while applying sonication to said aqueous medium.

2. The method of claim 1 wherein said reducing agent is ethylene.

3. The method of claim 1 wherein said reducing agent is sodium dodecyl sulfate (SDS).

4. The method of claim 1 wherein said reducing agent is poly(oxyethylene(20) sorbitan monolaurate).

5. The method of claim 1 wherein said porous support is initially impregnated with a single solution of water-soluble palladium and gold salts containing all the palladium and gold desired in the final catalyst, the palladium and gold are fixed as water-insoluble compounds on the support in a single fixing step by contacting said impregnated support with a solution of said alkaline compound, and said water-insoluble palladium and gold compounds are reduced in a single reducing step to their free metallic form while carrying out said sonication.

6. The method of claim 1 wherein said porous support is initially impregnated with an aqueous solution of a water-soluble palladium salt, said palladium is fixed on the support by immersing said impregnated support in a solution of an alkaline compound capable of reacting with said palladium salt to form a water-insoluble palladium compound, the support containing the fixed palladium is separately impregnated with a water-soluble gold salt, the gold is fixed by reaction with an alkaline fixing compound and the palladium and gold are reduced to their free metallic form, while carrying out said sonication.

7. The method of claim 1 wherein an alkali metal acetate is deposited on the catalyst after the deposition on the support of said palladium and gold in free metallic form.

8. The method of claim 7 wherein said alkali metal acetate is potassium acetate.

* * * * *